United States Patent
Desjardins et al.

(10) Patent No.: US 9,757,034 B2
(45) Date of Patent: Sep. 12, 2017

(54) FLEXIBLE TETHER WITH INTEGRATED SENSORS FOR DYNAMIC INSTRUMENT TRACKING

(75) Inventors: Adrien Emmanuel Desjardins, Eindhoven (NL); Gert Wim 'T Hooft, Eindhoven (NL); Raymond Chan, San Diego, CA (US); Robert Manzke, Sleepy Hollow, NY (US); Guy Shechter, Briarcliff Manor, NY (US); Christopher Stephen Hall, Hopewell Junction, NY (US)

(73) Assignee: Koninklijke Philips N.V., Eindhoven (NL)

( * ) Notice: Subject to any disclaimer, the term of this patent is extended or adjusted under 35 U.S.C. 154(b) by 593 days.

(21) Appl. No.: 13/877,343

(22) PCT Filed: Oct. 6, 2011

(86) PCT No.: PCT/IB2011/054400
§ 371 (c)(1),
(2), (4) Date: Apr. 2, 2013

(87) PCT Pub. No.: WO2012/046202
PCT Pub. Date: Apr. 12, 2012

(65) Prior Publication Data
US 2013/0188855 A1 Jul. 25, 2013

Related U.S. Application Data

(60) Provisional application No. 61/391,137, filed on Oct. 8, 2010.

(51) Int. Cl.
A61B 6/00 (2006.01)
A61B 5/00 (2006.01)
(Continued)

(52) U.S. Cl.
CPC .......... *A61B 5/0033* (2013.01); *A61B 6/4494* (2013.01); *A61B 34/20* (2016.02);
(Continued)

(58) Field of Classification Search
CPC . A61B 5/0033; A61B 6/4494; A61B 17/3478; A61B 9/5244; A61B 2019/448;
(Continued)

(56) References Cited

U.S. PATENT DOCUMENTS 4,821,727 A * 4/1989 Levene et al. ................ 600/407
5,638,819 A 6/1997 Manwaring et al.
(Continued)

FOREIGN PATENT DOCUMENTS

JP 2001178734 A 7/2001
JP 2010104426 A 5/2010
(Continued)

OTHER PUBLICATIONS

Machine translation of Chinese Office Action for CN201180048443, Issued Dec. 9, 2015.*
(Continued)

*Primary Examiner* — Katrina Fujita

(57) ABSTRACT

A system and method are provided for tracking a functional part of an instrument during an interventional procedure and displaying dynamic imaging corresponding to a functional part of the instrument. The system comprises: at least one instrument; a system for acquiring anatomical images relevant to guiding the instrument; a tether connected to the imaging system at a fixed end and connected to the instrument at a distal end, the tether comprising at least one longitudinal optical fiber with a plurality of optical shape sensors; an optical console that interrogates the sensors and detects reflected light; and a processor that calculates local curvature at each sensor location to determine the three-
(Continued)

dimensional shape of the tether and determines the location and orientation of the instrument relative to the images using the local curvatures of the tether and the location of the fixed end of the tether.

20 Claims, 6 Drawing Sheets

(51) Int. Cl.
 A61B 34/20 (2016.01)
 A61B 90/98 (2016.01)
 A61B 17/34 (2006.01)
 A61B 90/00 (2016.01)
(52) U.S. Cl.
 CPC .......... *A61B 90/98* (2016.02); *A61B 17/3478* (2013.01); *A61B 2034/2061* (2016.02); *A61B 2090/3764* (2016.02)
(58) Field of Classification Search
 CPC .... A61B 2019/5242; A61B 2019/5261; A61B 34/20; A61B 2034/2061; A61B 90/98; A61B 2090/3764
 See application file for complete search history.

(56) References Cited

U.S. PATENT DOCUMENTS

| | | | |
|---|---|---|---|
| 6,346,940 B1 | 2/2002 | Fukunaga | |
| 6,522,906 B1 | 2/2003 | Salisbury et al. | |
| 6,850,794 B2 | 2/2005 | Shahidi | |
| 7,319,877 B2 | 1/2008 | Krumm et al. | |
| 7,643,862 B2 * | 1/2010 | Schoenefeld | 600/407 |
| 7,720,322 B2 | 5/2010 | Prisco | |
| 8,211,010 B2 | 7/2012 | Hirakawa | |
| 8,337,397 B2 * | 12/2012 | Prisco et al. | 600/117 |
| 9,285,246 B2 * | 3/2016 | Prisco | G01D 5/35316 |
| 2001/0027263 A1 | 10/2001 | Zylka et al. | |
| 2001/0027272 A1 | 10/2001 | Saito et al. | |
| 2003/0088179 A1 | 5/2003 | Seeley et al. | |
| 2003/0114730 A1 | 6/2003 | Hale | |
| 2004/0133189 A1 | 7/2004 | Sakurai | |
| 2004/0234218 A1 * | 11/2004 | Tao | B29D 11/00721 385/126 |
| 2005/0113643 A1 | 5/2005 | Hale | |
| 2006/0013523 A1 | 1/2006 | Childlers et al. | |
| 2007/0156019 A1 | 7/2007 | Larkin et al. | |
| 2008/0262654 A1 | 10/2008 | Omori et al. | |
| 2009/0137952 A1 | 5/2009 | Ramamurthy et al. | |
| 2010/0030063 A1 | 2/2010 | Lee et al. | |
| 2010/0076455 A1 | 3/2010 | Birkenbach et al. | |
| 2010/0249506 A1 * | 9/2010 | Prisco | A61B 1/00009 600/117 |
| 2010/0249507 A1 | 9/2010 | Prisco et al. | |
| 2011/0113852 A1 * | 5/2011 | Prisco | A61B 19/2203 73/1.15 |
| 2016/0151121 A1 * | 6/2016 | Prisco | G01D 5/35316 606/130 |
| 2016/0157944 A1 * | 6/2016 | Prisco | G01D 5/35316 606/130 |

FOREIGN PATENT DOCUMENTS

| | | | | |
|---|---|---|---|---|
| WO | WO 2008/053402 | * | 5/2008 | ............... A61B 6/03 |
| WO | WO2008097540 | | 8/2008 | |
| WO | 2010111090 A1 | | 9/2010 | |

OTHER PUBLICATIONS

Machine translation of Japanese Office Action for JP2013-532306, Issued Aug. 3, 2015.*

* cited by examiner

FLEXIBLE TETHER WITH INTEGRATED SENSORS FOR DYNAMIC INSTRUMENT TRACKING

The invention relates to the field of medical imaging and more particularly to tracking a functional part of an instrument and providing dynamic imaging corresponding to the functional part of the instrument.

Imaging systems are increasingly used to guide instruments during intervention procedures. In current practice, volumetric imaging performed with modalities such as Magnetic Resonance Imaging (MRI), Computed Tomography (CT), or XperCT (e.g. live fluoroscopy images co-registered with flat detector CT images) can be used to identify the locations of tissue targets prior to a procedure and to identify sensitive tissues surrounding the targets in order to minimize complications resulting from collateral tissue damage. These image volumes may be acquired with different modalities than those used to guide instruments used in a procedure in real-time. For example, CT may be used for pre-procedural imaging, and ultrasound may be used for real-time image guidance.

Accurate localization of the functional parts of instruments (for instance the blade of a scalpel) relative to structures that were identified on pre-procedural images is critical to physicians. Often there is limited information available for real-time image guidance. The available information may be limited because the use of imaging techniques is kept to a minimum (e.g. to reduce patient exposure to ionizing radiation when using x-ray fluoroscopy). The available information also may be limited due to inherent limitations of the imaging technique (e.g. lack of contrast for some lesions on ultrasound). Therefore, physicians often experience uncertainties about the locations of the instruments relative to the anatomy revealed by the image volumes. These uncertainties can result in increased patient risks as well as elevated procedural costs.

A number of marker-based approaches for instrument tracking have been proposed. One such marker-based approach is optical tracking. In optical tracking, markers are placed on an instrument in such a way that they are visible with optical detectors. In this method, objects that block, obscure, or otherwise limit the field-of-view and line-of-sight of the detectors can disable the algorithm or degrade its tracking performance.

Another marker-based approach is electromagnetic (EM) guidance. This method requires placing EM sensors on the instrument. While line-of-sight problems encountered with optical tracking do not apply to this method, tracking accuracy and precision can be degraded by external EM fields due to spatiotemporal variations in the EM environment.

In both of the above-mentioned marker-based tracking approaches, the position of the markers must be registered to the coordinate system of the image volumes. Errors can arise in cases where there are mis-registrations between these coordinate systems. Mis-registrations can arise when the EM system moves slightly within the room, for example.

Another approach is the use of optical shape sensing to determine the shape of an elongated flexible instrument, such as a catheter within an anatomical structure. Optical shape sensing in this context refers to the delivery of light to optical fiber cores positioned in the instrument and the collection of light from optical fiber cores positioned in the instrument; signals pertaining to collected light are processed to infer the shape or aspects of the shape of the instrument or aspects of the shape of this instrument. Optical shape sensing can involve backscattering from Fiber Bragg Gratings ("FBGs") as well as Rayleigh scatterers in the cores or cladding of optical fibers, for instance. This shape sensing is described in conjunction with a marker-based approach. In this approach, a marker is placed on the instrument for tracking the instrument's location and optical shape sensing is used to determine the shape of the instrument within an anatomical structure.

A system and method are provided for tracking a functional part of an instrument during an intervention procedure by determining the three-dimensional shape of a tether connecting the instrument to an imaging system, and displaying dynamic imaging corresponding to the functional part of the instrument.

According to one embodiment the system comprises: at least one instrument; a system for acquiring anatomical images relevant to guiding the instrument; a tether connected to the imaging system at a fixed end, connected to the instrument at a distal end, and comprising at least one longitudinal optical fiber with a plurality of optical sensors comprising optical fiber cores with scattering sources such as Fiber Bragg Gratings or Rayleigh scatterers; an optical console that interrogates the sensors and detects reflected light, and a processor that calculates local curvature along the lengths of the sensors to determine the three-dimensional shape of the tether and determines the location and orientation of the instrument relative to the images using the three-dimensional shape of the tether and the location of the fixed end of the tether. In one embodiment there are four fiber cores with one fiber core on-axis and the others arranged in a helical fashion around the on-axis fiber core. Although the invention is discussed herein with regard to FBGs, it is understood to include fiber optics for shape sensing or localization generally, including, for example, with or without the presence of FBGs or other optics, sensing or localization from detection of variation in one or more sections in a fiber using back scattering, optical fiber force sensing, fiber location sensors or Rayleigh scattering.

According to one embodiment the imaging system constructs a three-dimensional image space and displays an appropriate view of the image space for the instrument, showing the functional part of the instrument in the image space.

In one embodiment the instrument is selected from a plurality of instruments. In this embodiment, the system further comprises an instrument identification unit identifying a selected one of the plurality of instruments. The identification unit may be an RFID receiver, wherein an RFID transmitter identifying the instrument is disposed on the instrument or on packing for the instrument. Alternatively, the identification unit may be a bar code reader, wherein a bar code identifying the instrument is disposed on the instrument or on packing for the instrument. According to another alternative embodiment, the identification unit is an electrical sensor and an electrical signal identifying the instrument is provided by the instrument or by packaging for the instrument. In yet another alternative embodiment the identification unit is a keypad for manual entry of an identification indication.

According to one embodiment the processor is an image processor of the imaging system.

According to one embodiment the instrument is removably connected to the distal end of the tether by a mechanical connection, such as a collar or threaded engagement. Alternatively, the instrument may be removably connected to the distal end of the tether by a magnetic connection or an adhesive.

The imaging system may be an XperCT system, wherein the tether is connected to a C-arm body of the XperCT system. Alternatively, the imaging system may be a combined X-ray breast mammography and biopsy system, wherein the tether is connected to an X-ray source, an X-ray detector, or a biopsy system.

According to one embodiment at least two tethers are connected to the imaging system. This allows for tracking two instruments simultaneously.

According to one embodiment, at least one marker is disposed on the tether or on the instrument to provide real-time reference points for calculating the shape of the tether.

The marker may be a radio-opaque marker. Alternatively, the marker may be an electromagnetic or optical marker. The optical fiber cores are integrated in the tether. Preferably there are four optical fiber cores, with one fiber core on-axis and the others arranged in a helical fashion around the on-axis fiber core. It should be noted that the four cores could either be contained within a single fiber (thereby sharing the cladding) or in separate fibers mechanically connected (e.g. glued).

According to one embodiment a method is provided for tracking a functional part of an instrument and displaying dynamic imaging corresponding to a functional part of the instrument. The method comprises: receiving imaging data from an imaging machine; constructing an image volume; determining a three-dimensional shape of a flexible tether having one end fixed at a known location relative to the imaging machine and having an instrument connector disposed at an opposite end; determining a location of the functional part of the instrument using the known location of the fixed end of the tether, the three-dimensional shape of the tether, and a pre-determined size and shape of the instrument; and displaying a dynamic image corresponding to the instrument and showing the functional part of the selected instrument in the image volume.

According to one embodiment the flexible tether comprises fiber optic cores disposed longitudinally in the tether. A plurality of optical scatterers (e.g. Fiber Bragg Gratings or Rayleigh scatterers) are disposed in optical fiber cores or claddings. The reflectivity at different locations along the tether is measured. From these length-resolved reflectivity measurements, length-resolved strain and curvature calculations are made. From the latter, the three dimensional shape of the tether is calculated.

According to one embodiment the instrument is selected from a plurality of instruments. The method of this embodiment further comprises receiving identification of a selected instrument attached to the instrument connector selected from a plurality of instruments. In one embodiment, the instrument is removed, a new instrument is attached to the tether, and the new instrument is identified by the instrument identification unit.

According to one embodiment, the method further comprises refining the shape calculations for the tether using real-time imaging.

The features and advantages of the invention will be more clearly understood from the following detailed description of the preferred embodiments when read in connection with the accompanying drawing. Included in the drawing are the following figures.

The present invention provides a method and system for markerless tracking of an instrument during an intervention procedure and for displaying an image space corresponding to the selected instrument and showing the functional part of the selected instrument in the image space.

Figure 1:
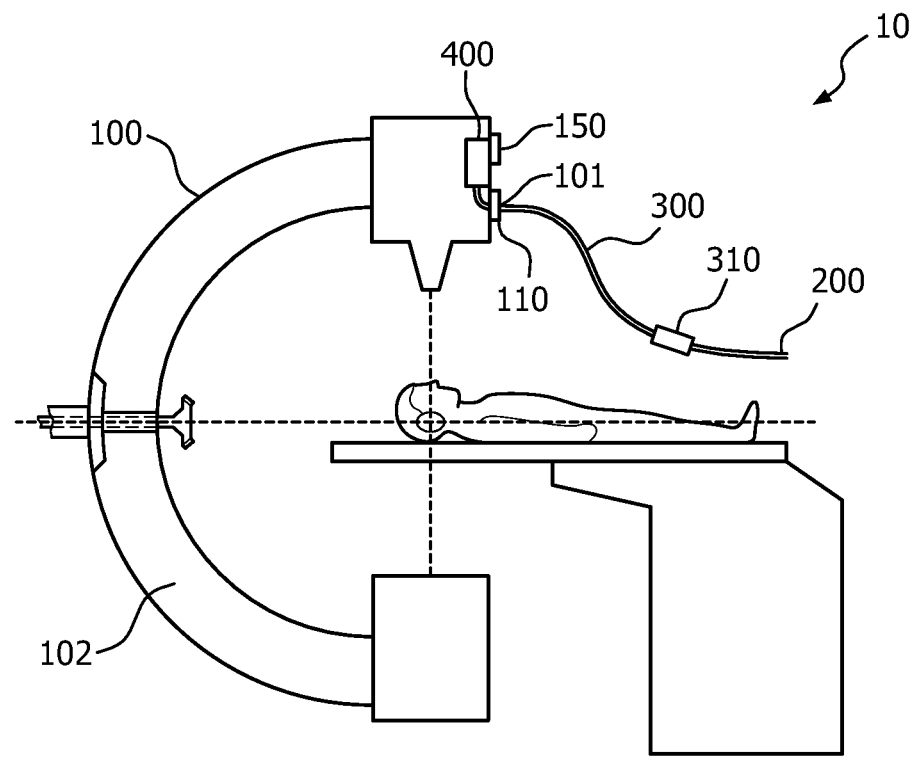
FIG. 1 is a side view of a markerless tracking system according to an embodiment of the present invention.
Figure 2:
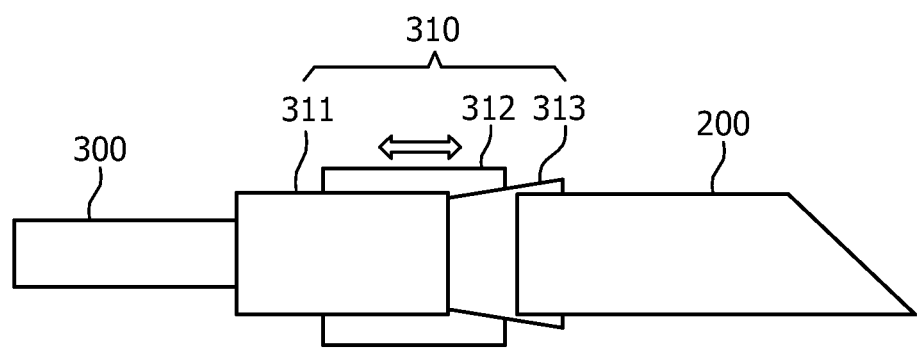
FIG. 2 is a sectional view of a connector for attaching an instrument to a tether of a markerless tracking system according to an embodiment of the present invention.

According to one embodiment of the present invention, an instrument tracking system 10 comprises an imaging system 100 used to acquire and display an image space showing anatomical structures proximate to an intervention procedure to be performed. The imaging system 100 may be a C-arm flat-detector CT imaging system as shown in FIG. 1. Alternatively, the imaging system may be an MRI, CY, X-ray, ultrasound, or any other type of imaging system appropriate for acquiring images of anatomic structures for use in guiding an instrument during an intervention procedure. According to one embodiment, the imaging system 100 is an imaging system capable of providing a three-dimensional image volume.

The instrument tracking system 10 also comprises an instrument 200 for use in an intervention procedure. The instrument may be any instrument used during an intervention, including but not limited to: a mechanical scalpel (lancet), a laser scalpel, an endoscope, microscopic imaging probes, a surgical stapler, a retractor, a cautery device (electrical or optical), a catheter, a chisel, a clamp, a probe, a trocar, scissors, or the like. The instrument 200 is manipulated by a physician to perform an intervention procedure. In many intervention procedures, a physician will use more than one instrument. Therefore, according to one embodiment, the instrument tracking system comprises more than one instrument.

The instrument 200 (or one of the instruments) is connected to a connection point 101 on the imaging system 100 by a tether 300. The connection point 101 is a point that can be registered to the coordinates of the image space of the imaging system 100. According to one embodiment, the connection point is at an optical connector 110. In the illustrated embodiment, the optical connector 110 is fixed on the C-arm body of the CT imaging system.

The instrument 200 is connected to the tether 300 by a connector 310. According to one embodiment, the connector 300 uses clamping force to hold the instrument firmly in place. The connector 310 comprises a cylinder 311 fixedly connected to the tether 300 by crimping, adhesive, or any other appropriate fastening method. The cylinder may be plastic or any other suitable radiolucent structural material.

The cylinder 311 has an external thread which is engaged with an internal thread on a collar 312. The collar may also be plastic or any other suitable radiolucent structural material. A tapered flexible wrap 313 extends into the collar opposite the tether 300 and is affixed to the cylinder 311 by adhesive, clamping, or any other suitable fixation method. The flexible wrap may be rubber or any other radiolucent flexible material suitable for deforming and clamping an instrument. The instrument 200 is placed into the open tapered flexible wrap 313 and may be abutted to a flange on the cylinder 311 for precision location of the instrument 200 relative to the tether 300. The collar 312 is rotated about the cylinder 311 advancing the collar 312 along its axis away from the tether 300 and pressing on the tapered flexible wrap 313 to securely hold the instrument 200 in place.

The connector 310 allows a physician to attach any one of a plurality of instruments 200 to the tether 300. Moreover, the connector 310 allows the physician to change instruments during an intervention procedure, as will be described hereafter.

According to alternative embodiments, the instrument 200 may be connected to the tether 300 by adhesive, a magnetic connection, threaded engagement of the instrument directly to the tether 300 or a threaded member attached to the tether, or any other suitable connection method.

The tether 300 comprises optical fiber cores 324 (FIG. 3), which together with an optical console 400 (FIG. 1) form a shape sensing system 320 that provides strain information. This strain information can be used to determine the precise location of the instrument 200 and to present the instrument location on an image from the imaging system 100.

Figure 3:
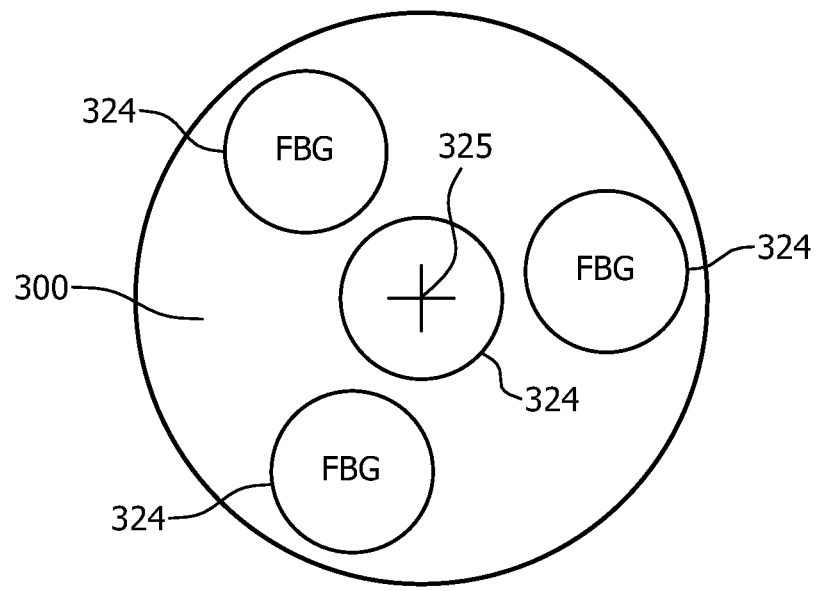
FIG. 3 is a sectional view of a tether of a markerless tracking system according to an embodiment of the present invention.

Within the tether 300, at least one and preferably four optical fibers 324 extend along the tether axis 325 as shown in FIG. 3. Preferably one fiber core is on-axis and the others arranged in a helical fashion around the on-axis fiber core. It should be noted that the four cores could either be contained within a single fiber (thereby sharing the cladding) or in separate fibers mechanically connected (e.g. glued). According to one embodiment, the optical fibers 324 are symmetrically arranged around the tether axis 325. A plurality of optical scatterers are provided in the optical fiber cores or claddings in a plurality of locations along the length of the tether 300 (a single Fiber Bragg grating is shown in FIG. 4).

A Fiber Bragg Grating is a segment of an optical fiber that reflects particular wavelengths of light and transmits all other wavelengths of light. This is achieved by adding a periodic variation of the refractive index in the fiber core, which generates a wavelength-specific dielectric mirror. A Fiber Bragg Grating can therefore be used as an inline optical filter to block certain wavelengths, or as a wavelength-specific reflector.

Figure 4:
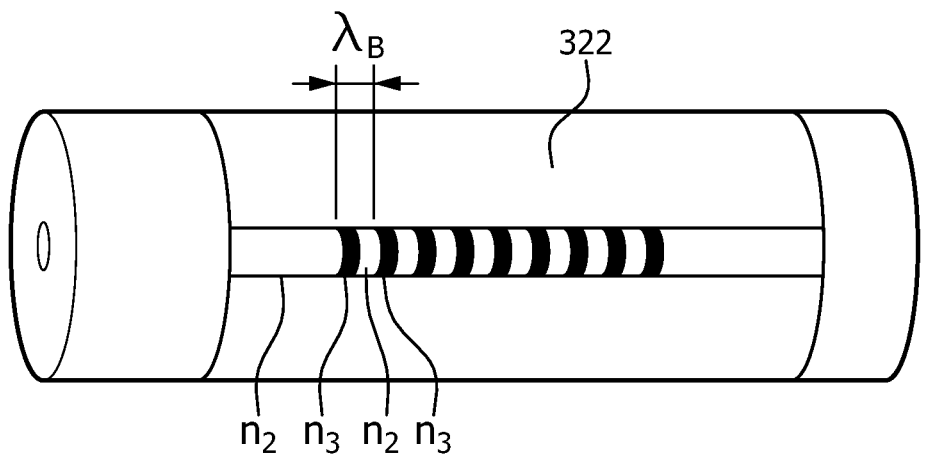
FIG. 4 is a sectional view of an optical fiber showing four optical cores according to an embodiment of the present invention.
Figure 5A:
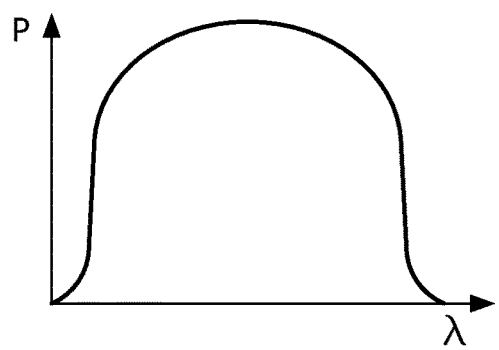
FIGS. 5A-5C are graphs of a spectral response for a Fiber Bragg Grating according to an embodiment of the present invention.
Figure 5B:
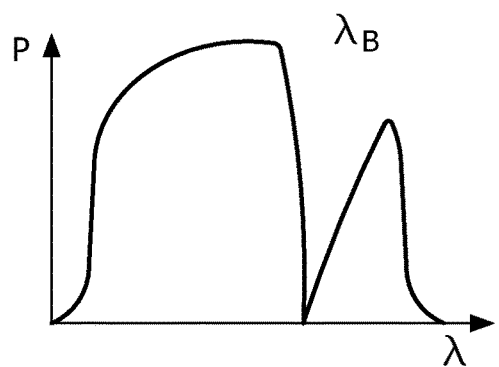
Figure 5C:
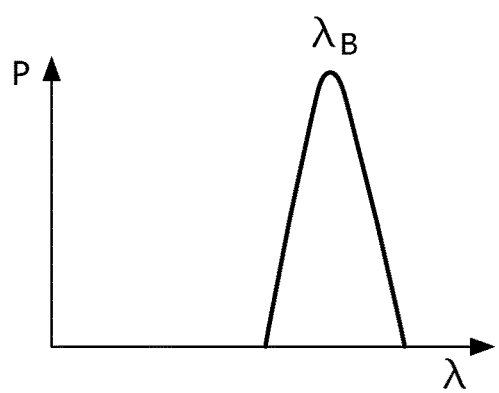

As shown in FIG. 4, the core of the optical fiber 324 has a refractive index of $n_2$ along most of its length. However, the refractive index is periodically changed to a different refractive index $n_3$ at a spacing of $\lambda_B/2n_{\text{eff}}$ (where $n_{\text{eff}}$ is the effective refractive index of the optical mode). FIGS. 5A-5C show the spectral response of a broadband light signal to the Bragg Grating. As shown in FIG. 5A, a broad spectrum light signal is input to the optical fiber 324. The light is split into light that is not at a wavelength $\lambda_B$ which is transmitted through the Bragg Grating (shown in FIG. 5B) and light at a wavelength of $\lambda_B$ which is reflected by the Bragg Grating (shown in FIG. 5C).

Fiber Bragg Gratings involve Fresnel reflections at each of the interfaces where the refractive index changes. For some wavelengths, the reflected light of the various periods is in phase with one another so that constructive interference exists for reflection and consequently, destructive interference for transmission.

The Bragg wavelength is sensitive to strain as well as to temperature. This means that Bragg gratings can be used as sensing elements in fiber optic sensors. In a FBG sensor, the measurand causes a shift in the Bragg wavelength $\lambda_B$. The relative shift In the Bragg wavelength, $\Delta\lambda_B/\lambda_B$, due to an applied strain ($\in$) and a change in temperature ($\Delta T$) is approximately given by:

$$\delta\lambda_B/\lambda_B = C_S \in + C_T \Delta T \quad (1)$$

The coefficient $C_S$ is called the coefficient of strain and its magnitude is usually around $0.8\times10^{-6}/\mu\in$ (or in absolute quantities about 1 pm/$\mu\in$). The coefficient $C_T$ describes the temperature sensitivity of the sensor; it is made up of the thermal expansion coefficient and the thermo-optic effect. Its value is around $7\times10^{-6}$/K (or in absolute quantity 13 pm/K).

Figure 6:
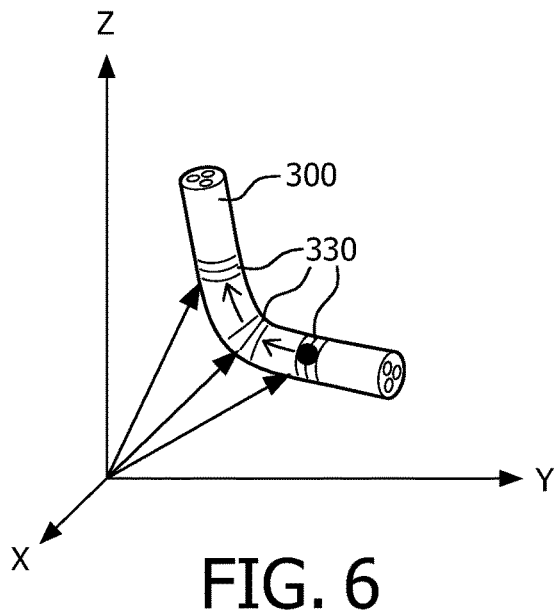
FIG. 6 is an isometric view of a section of tether showing curvature measuring sensors according to an embodiment of the present invention.

A plurality of optical scatterers 330 (e.g. Fiber Bragg Gratings or Rayleigh scatterers) can be distributed over the length of an optical fiber in the core or cladding to form sensors or gauges to measure strain. Incorporating at least four fiber optic cores with various sensors (gauges) along the length of a fiber that is embedded in a structure allows for the three-dimensional form of the structure to be precisely determined. As shown in FIG. 6, scatterers 330 are located at each of a plurality of positions along the length of the tether 300. The local curvature of the tether 300 can be determined from the length-resolved strain and curvature measurements acquired from the tether 300. The total three-dimensional form of the tether 300 is determined from the plurality of strain and curvature measurements.

According to one embodiment, multiple tethers can be used to simultaneously track multiple instruments in the coordinates of the image volume acquired from the imaging system 100.

Returning to FIG. 1, an optical console 400 is connected to the optical fiber cores 324 of the tether 300 at the connection point 101. In the illustrated embodiment, the optical console is mounted within the C-arm body of the imaging system 100. The optical console 400 delivers light to the optical fibers and/or fiber optic cores and receives light from them. In the case where Fiber Bragg Gratings are utilized, the optical console 400 can determine the Bragg wavelength $\lambda_B$ for different portions of each Fiber Bragg Grating 322.

According to one embodiment, an attachment means 150 is disposed on the C-arm of the imaging system 100 to secure the loose end of the tether 300 during rotational scans. The attachment means may be any mechanical connection device suitable for securing the tether 300.

Figure 7:
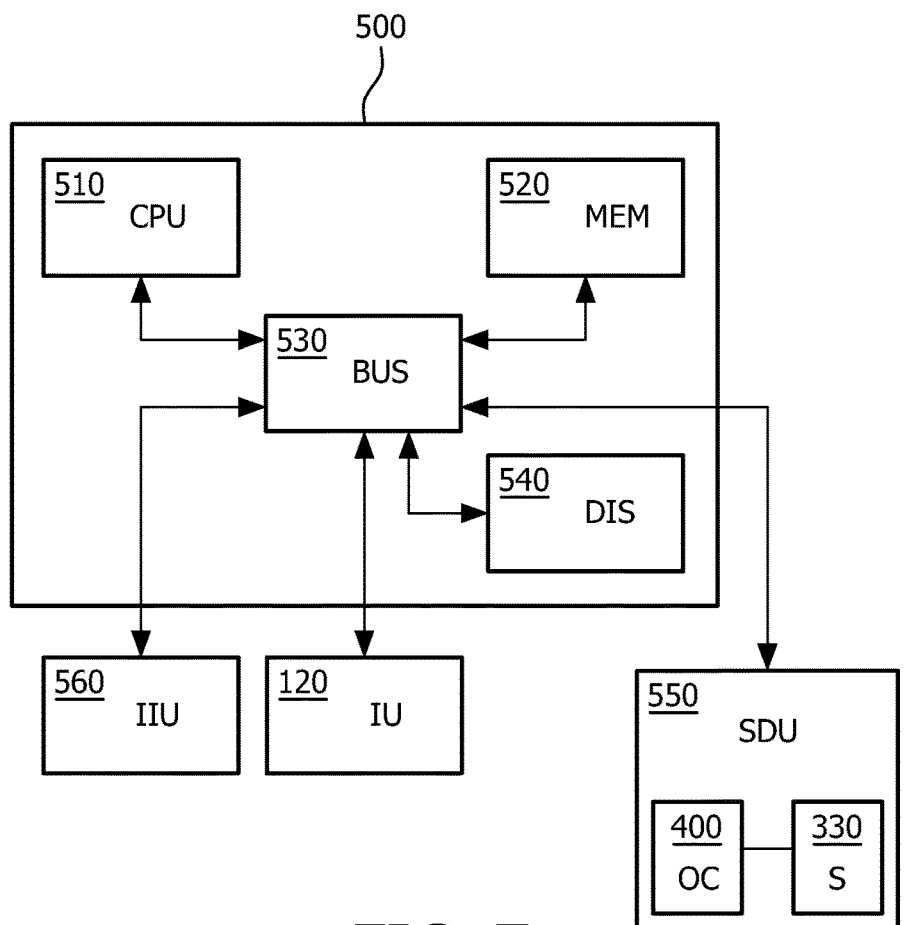
FIG. 7 is a block diagram of a markerless instrument tracking system according to an embodiment of the present invention.

FIG. 7 is a block diagram of the instrument guidance system 10 shown in FIG. 1. A processing unit 500 comprises a processor 510 which is operably connected to a memory 520. According to one embodiment, they are connected through a bus 530. The processor 510 may be may be any device capable of executing program instructions, such as one or more microprocessors. The memory may be any volatile or non-volatile memory device, such as a removable disc, a hard drive, a CD, a Random Access Memory (RAM), a Read Only Memory (ROM), or the like.

A display 540 is also operably connected to the processor 510. The display may be any monitor, screen, or the like suitable for presenting a graphical user interface (GUI) capable of presenting medical images.

An imaging unit 120, such as the C-arm 102 (in FIG. 1) of an imaging system 100, is operably connected to the processor 510. The imaging unit provides imaging data to the processor 510 for processing to create an image volume of anatomical features. The image volume is then presented on the display 540. The processing unit 500 and the imaging unit 120 together form an imaging system 100.

A shape determining unit 550 provides strain and curvature data from the tether 300 to the processor 510. The shape determining unit comprises the optical shape sensor (including optical fiber cores 324 that are located in the tether 300 along its longitudinal axis 325). The shape determining unit 550 further comprises an optical console 400, which interrogates the optical fiber cores sending a broadband light signal along each optical fiber core and measuring the reflected wavelengths to determine length-resolved strain and curvature in each optical fiber core. Alternatively, the reflection spectrum may be obtained from a narrow band light source whereby the wavelength is swept in time. The localized curvatures are used to determine the shape of the tether 300 within the image space.

The optical console 400 may have a processor (not shown) separate from the processor 510 in the processing unit 500. Moreover, the optical module 400 may perform some or all of the calculations for wavelength shift, strain, and curvature; and provide wavelength measurements, shift calculations, strain calculations, or curvature data to the processor 510. The processor 510 processes imaging data to form an image space which is presented on the display 540. The data from the shape determining unit 550 is processed, as necessary to calculate curvatures over the length of the tether 300. This shape data is used by the processor 510, together with the known registration point 101 at the fixed end of the tether 300 (FIG. 1) to determine the location and orientation of the tether 300 at the connection 310, and therefore the location and orientation of the instrument 200 in the image space.

An Instrument Identification Unit (IIU) 560 is operably connected to the processor 510 in the processing unit 500. The IIU 560 comprises means for identifying one of a plurality of instruments 200 in use by a physician during an intervention procedure. The identifying means may comprise a Radio Frequency Identification (RFID) receiver, with each instrument 200 or its packaging having an RFID transmitter attached to it. Alternatively, the identifying means may be a bar code reader, with each instrument 200 or its packaging having a bar code printed on it. According to another embodiment, a resistance code or microchip may be embedded in or attached to each instrument 200. According to yet another embodiment, the identifying means may be a keyboard or keypad, with the physician manually entering an identification indication, such as a code, or selecting from a menu, or the like. The identifying means may be integral with the connector 310 such that the identification information is transmitted through the tether 300. Alternatively, the identifying means may be disposed at another location, such as the processing unit with the instrument 200 brought to the identifying means for identification.

Figure 8:
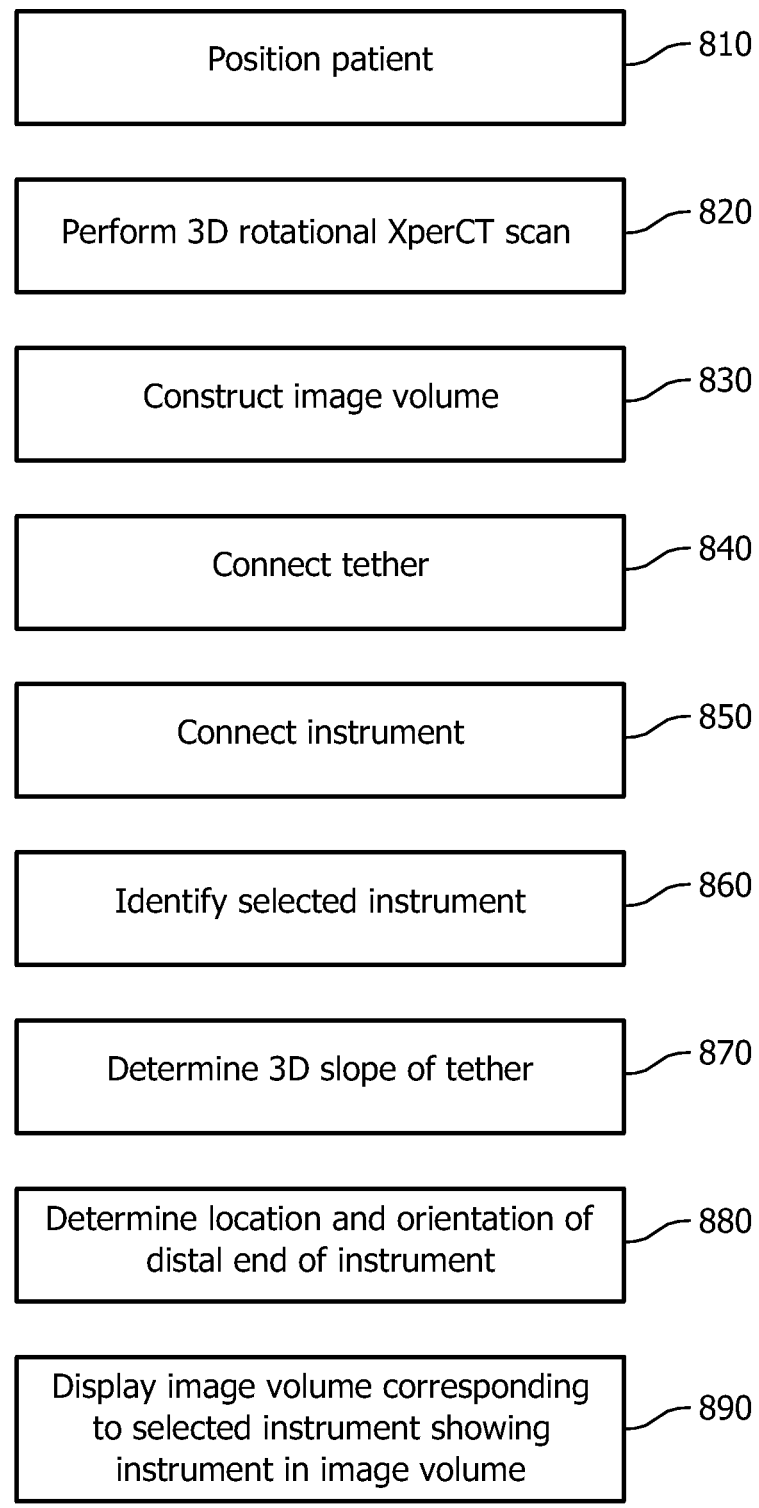
FIG. 8 is a flow diagram of a method for tracking an instrument in an image space without markers according to an embodiment of the present invention.

Referring now to FIG. 8, a flow diagram is shown for a method for dynamically tracking an instrument in an image space. A patient is positioned on an imaging system 100 (step 810). Patient positioning is performed according to known procedures in the art. According to one embodiment, the patient is positioned on an XperCT imaging system within the C-arm body as shown in FIG. 1.

A three-dimensional rotational XperCT scan is performed on the patient (step 820). The scan is performed according to known procedures in the art. It should be understood that alternate embodiments are contemplated using forms of imaging other than the three-dimensional rotational XperCT scan. Moreover, a scan may be performed before a procedure, during a procedure, or both.

The processor 510 constructs an image volume from the scan data (step 830). The image volume is constructed using procedures known in the art showing anatomical structures.

A physician connects the tether 300 to the imaging unit of the imaging system 100 at the connection point 101 (step 840). Connection point 101 is a location that can be registered to the image volume. That is, the location of the connection point is known relative to the image volume. An optical connector 110 is provided at the connection location 101. According to one embodiment, the connection point 101 is located on the C-arm body of a XperCT imaging system. In another embodiment, a connection point may be at a source or detector for an imaging system.

The physician connects the tether 300 to the imaging system 100 (step 850). The tether is installed in the optical connector 110, which is connected by optical fibers to the optical console 400. According to one embodiment, the tether 300 is connected after the scan is performed. According to another embodiment, the tether 300 is connected prior to a scan and secured to the imaging system 100 at its distal end using attachment means 150.

An instrument identification unit 560 identifies a selected instrument 200 (step 860). As previously described, the instrument identification unit 560 may be an RFID receiver, a bar code reader, a keyboard or keypad, an electrical sensor, or any other means suitable for providing a code or signal to indicate a selected one of a plurality of instruments 200. The RFID transmitter, bar code, or the like may be provided on the selected instrument 200 or on its packaging. In the RFID example, the physician takes the instrument 200 or packaging with the RFID transmitter and places it in proximity to the RFID receiver of the instrument identification unit 560. The RFID receiver of the instrument identification unit 560 receives the RFID signal and transmits the RFID code to the processor 510. Alternatively, a processor separate from the imaging processor 510 may receive the identification code. In an alternative embodiment, the physician enters an instrument 200 identification code using a keyboard, keypad, or the like.

The processor 510 determines the shape of the tether 300 (step 870). Using known calculation methods, the known connection point 101, and the curvature data from each sensor triplet 330 along the length of the tether 300, the imaging processor 510 calculates the complete three-dimensional shape of the tether and registers it to the image volume. According to alternate embodiments, a processor separate from the image processor 510 determines the shape of the tether 300. Also, according to various embodiments, the strain calculations and curvature calculations may be performed by the imaging processor 510, another processor, or a combination thereof. Alternatively, the processor could calculate the complete three-dimensional shape of a portion of the tether that is clinically relevant; this portion of the tether could be localized relative to the imaging system or another structure by means of one or more markers that are positioned on the tether and tracked with known methods that do not involve the optical fibers or optical fiber cores described in this invention (e.g. EM tracking).

The processor 510 determines the location and orientation of the functional part of the selected instrument 200 (step 880). Once the three-dimensional shape of the tether, the connection point 101, and the identification of the selected instrument 200 are known, the image processor 510 determines the location of the functional part of the selected instrument 200 and the orientation of the selected instrument 200 in the image space. This determination is performed using a preprogrammed shape and size for the selected instrument 200.

The processor 510 displays the image volume of the patient corresponding to the selected instrument showing the instrument in the image volume (step 890). Different views of the image volume would be more appropriate for different instruments 200. For example, for a procedure that involves a needle insertion, an image volume in which critical structures such as blood vessels are segmented and highlighted might be appropriate. As another example, for a procedure that involves removing brain tumor tissue with a scalpel or suction device, an image volume in which tumor tissue is segmented and highlighted might be appropriate. The processor 510 displays an image most useful or corresponding to which instrument 200 is selected. The processor 510 shows the selected instrument 200 in the image.

The displayed image may be from a pre-procedural scan or a scan performed during a procedure. For example, a pre-procedural image may be acquired using CT or MRI. Following the imaging, the patient is moved to a surgical table, where an XperCT image is acquired (rotational C-arm scan). The XperCT image is co-registered with the CT and/or MRI images. Two-dimensional flouroscopic images may be acquired in real-time and registered with the pre-procedural and XperCT images, such as for tracking (or refining) the depth of a scalpel.

In another example, no pre-procedural images are acquired. The patient is moved to a surgical table, where an XperCT image is acquired before the procedure starts (rotational C-arm scan), and potentially at different time points during the procedure. Optionally, fluoroscopic images may be acquired in real-time and registered to the XperCT images.

In another example, no pre-procedural images are acquired. The patient is moved to a surgical table with an open MRI. A MRI image is acquired before the procedure and potentially at different time points during the procedure.

In each of the foregoing procedures, the functional part of the instrument 200 can be registered to any of the acquired images, because the tether 300 is fixed at a location that is defined relative to the images (being a fixed location on the imaging equipment) and the three-dimensional shape of the tether 300 can be calculated, giving the location of the instrument 200. The selected instrument 200 is identified, so that the size and shape can be retrieved from memory and used to determine the precise location of the functional part of the instrument. Also, the selected instrument 200 may change during a procedure. For example, a physician may switch from a scalpel to a stapler. Since the new selected instrument 200 is identified, as previously described, the location of the functional part of the new selected instrument 200 can be determined with respect to the image space and an appropriate image can be presented showing the new selected instrument 200.

According to an alternative embodiment, at least one radio-opaque marker is disposed on the tether 300 or on the selected instrument 200. The radio-opaque marker is visible under two-dimensional fluoroscopy. When 2D fluoroscopy is utilized during a surgical intervention, the position of the marker(s) in a plane perpendicular to the x-ray detector-emitter axis can be determined in real-time. This determination can be performed by digital analysis of the fluoroscopic images, using image pattern recognition algorithms that are well-known in the scientific community. The marker positions can be utilized as reference points to improve the accuracy at which the 3D shape of the tether 300 and location of the instrument 200 are calculated.

According to another alternate embodiment, at least one electromagnetic (EM) or optical marker is disposed on the tether 300 or on the selected instrument 200. The marker positions, as determined by EM or optical sensors, are utilized as reference points to improve the accuracy at which the 3D shape of the tether 300 and/or instrument 200 is calculated.

Figure 9:
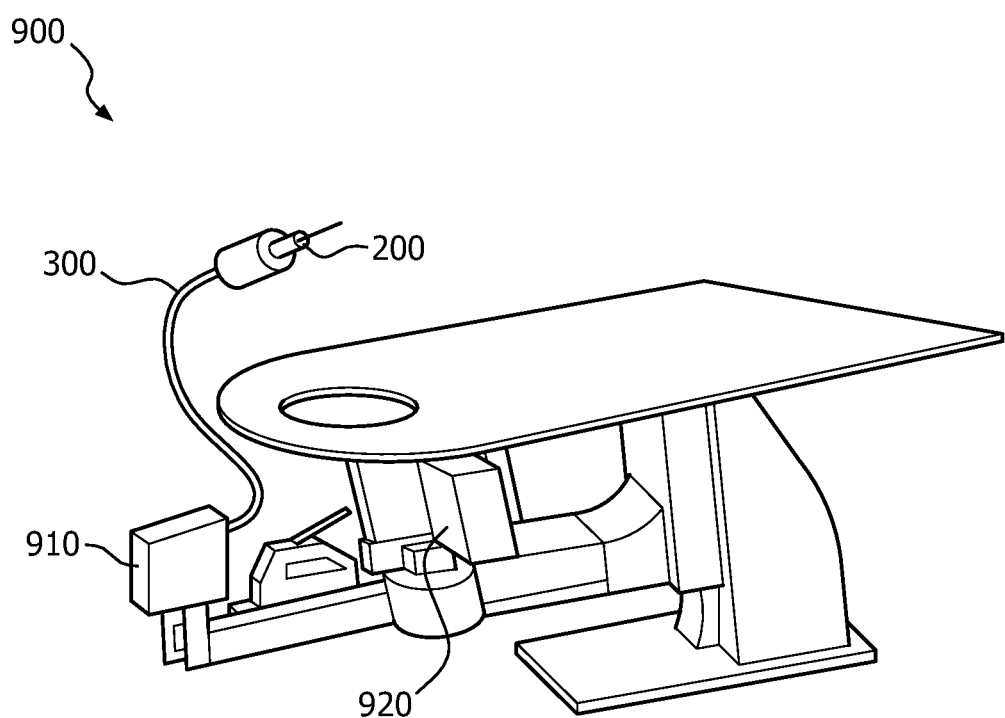
FIG. 9 is a side view of a markerless tracking system according to an alternative embodiment of the present invention.

Referring now to FIG. 9, a shape-sensing tether 300 is rigidly attached to a combined X-ray breast mammography/biopsy system 900. The tether is connected at either the X-ray source 910, the detector 920, the biopsy system, or any other rigid transformation point.

Breast mammography systems are able to obtain depth information on tumor nodules by performing tomosynthesis imaging, which involves moving a camera and detector around an object (in this case a breast). Based on images created using this procedure, depth information on tumor location is obtained which is later used for guided or automated breast biopsy.

Using a shape-sensing tether 300, a conventional, markerless, biopsy needle is tracked and placed with excellent accuracy based on the previously acquired tomosynthesis images. Since the tether 300 is mechanically connected to the combined imaging/biopsy system 900, the position of the instrument connector 310, and therefore the biopsy needle, as calculated with the shape determining algorithm is automatically registered to the coordinates of the tomosynthesis X-ray images.

The use of an optical shape sensing system in this particular application has the significant advantage that it is not sensitive to EM distortions that occur when using EM tracking. EM distortions occur due to metal, which is omnipresent in current X-ray mammography/biopsy systems.

The preceding description and accompanying drawing are intended to be illustrative and not limiting of the invention. The scope of the invention is intended to encompass equivalent variations and configurations to the full extent of the following claims.

What is claimed is:

1. A system for tracking a functional part of an instrument during an interventional procedure and displaying dynamic imaging corresponding to a functional part of the instrument, comprising:
   at least one instrument;
   a system for acquiring anatomical images relevant to guiding the instrument: a tether connected to the imaging system at a fixed end and connected to the instrument at a distal end, the tether comprising optical shape sensors;
   an optical console that interrogates the optical shape sensors; and
   a processor that calculates local curvature at different positions along the tether, determines the three-dimensional shape of the tether using the determined local curvatures, determines the location and orientation of the instrument relative to the images using the determined shape of the tether and the location of the fixed end of the tether and displays an appropriate view of the image space for the instrument, showing the functional part of the instrument in the image space.

2. The system of claim 1, wherein the imaging system constructs a three-dimensional image space.

3. The system of claim 1, wherein the instrument is selected from a plurality of instruments, the system further comprising an instrument identification unit identifying a selected one of a plurality of instruments.

4. The system of claim 3, wherein the identification unit is an RFID receiver and an RFID transmitter identifying the instrument is disposed on the instrument or on packing for the instrument.

5. The system of claim 3, wherein the identification unit is a bar code reader and a bar code identifying the instrument is disposed on the instrument or on packing for the instrument.

6. The system of claim 3, wherein the identification unit is an electrical sensor and an electrical signal identifying the instrument is provided by the instrument or by packing for the instrument.

7. The system of claim 3, wherein the identification unit is a keypad for manual entry of an identification indication.

8. The system of claim 1, wherein the processor is an image processor of the imaging system.

9. The system of claim 1, wherein the instrument is removably connected to the distal end of the tether by a mechanical connection.

10. The system of claim 1, wherein the instrument is removably connected to the distal end of the tether by a magnetic connection.

11. The system of claim 1 wherein the imaging system is an XperCT system, and the tether is connected to a C-arm body of the XperCT system.

12. The system of claim 1, wherein the imaging system is a combined X-ray breast mammography and biopsy system, and the tether is connected to an X-ray source, an X-ray detector, or a biopsy system.

13. The system of claim 1, wherein at least two tethers are connected to the imaging system.

14. The system of claim 1, wherein at least one marker is disposed on the tether or on the instrument to provide real-time reference points for calculating the shape of the tether.

15. The system of claim 14, wherein the marker is a radio-opaque marker.

16. The system of claim 1, wherein the optical shape sensor consists of at least one optical fiber with at least one optical fiber core having embedded optical scatterers.

17. The system of claim 16, wherein the optical shape sensor comprises one optical fiber core on a longitudinal axis of the tether and three optical fiber cores arranged in a helical pattern around the longitudinal axis, each fiber core having embedded optical scatters.

18. The system of claim 16, wherein the optical scatters are Rayleigh scatterers in the cores or in claddings of the cores.

19. The system of claim 16, wherein the optical scatters are Fiber Bragg Gratings.

20. A method for tracking a functional part of an instrument and displaying dynamic imaging corresponding to a functional part of the instrument, comprising:
receiving imaging data from an imaging machine;
constructing an image volume;
determining a three-dimensional shape of a flexible tether having one end fixed to the imaging machine and having an instrument connector disposed at an opposite end;
determining a location of the functional part of the instrument using the known location of the fixed end of the tether, three-dimensional shape of the tether, and a pre-determined size and shape of the instrument; and
displaying a dynamic image corresponding to the instrument and showing the functional part of the selected instrument in the image volume.

* * * * *